United States Patent [19]

Glasl et al.

[11] 3,985,541
[45] Oct. 12, 1976

[54] PLANT GROWTH REGULATORS AND PROCESS OF REGULATING PLANT GROWTH

[75] Inventors: Johann Glasl, Solingen; Günter Kreienfeld, Dusseldorf-Holthausen; Hermann Kroke, Erkrath-Unterbach, all of Germany

[73] Assignee: Henkel & Cie G.m.b.H., Dusseldorf-Holthausen, Germany

[22] Filed: Oct. 16, 1974

[21] Appl. No.: 515,417

[30] Foreign Application Priority Data
Nov. 3, 1973 Germany............................ 2355027

[52] U.S. Cl. .................................................... 71/78
[51] Int. Cl.² ............................................ A01N 9/24
[58] Field of Search ....................................... 71/78

[56] References Cited
UNITED STATES PATENTS
3,900,307  8/1975  Abramitis .............................. 71/78

*Primary Examiner*—Joseph Paul Baust
*Attorney, Agent, or Firm*—Hammond & Littell

[57] ABSTRACT

At least water-emulsifiable plant growth regulators, especially for inhibiting the growth of sucker shoots of tobacco plants, consisting of fatty acid polyoxyethylene glycol ester mixtures obtained by ethoxylating fatty acids having from 6 to 12 carbon atoms with from 4 to 8 mols of ethylene oxide per mol of fatty acid; as well as the process of inhibiting the undesired growth of plants, particularly the growth of sucker shoots of tobacco plants, by the application of aqueous solutions or emulsions of the above plant growth emulsifiers to the plants.

8 Claims, No Drawings

PLANT GROWTH REGULATORS AND PROCESS OF REGULATING PLANT GROWTH

THE PRIOR ART

The size and quality of tobacco leaves can be considerably increased if the growth of the axillary or sucker shoots is inhibited to a great extent or totally prevented. In the past, a great number of plant growth regulators or plant growth inhibitors have been developed which have replaced the cumbersome removal of the shoots by hand. Thus, it is generally known that one can inhibit the aftergrowth of the axillary or sucker shoots by spraying with mineral oil as well as with emulsions of certain fat derivatives. Fat derivatives recommended for this purpose are, in particular, fatty alcohols and methyl esters of fatty acid having a carbon chain range of 8 to 12 carbon atoms. These compounds are not soluble in water, hence, for the preparation of emulsifiable concentrates, it becomes of special importance to choose the proper emulsifier. Most anionic and nonionic emulsifiers which are suitable for the emulsification of such compounds are insufficiently compatible with plants. The most useful emulsifiers for medium-chain fatty alcohols and methyl esters of medium-chain fatty acids are the polyoxyethylene glycol fatty alcohol ethers and polyoxyethylene glycol fatty acid alkanolamide ethers. However, as shown by experiments with tobacco plants, emulsions of the fat derivatives prepared with the above emulsifiers and applied to the tobacco plants to prevent the sprouting of axillary shoots, cause severe damage to the leaves of the treated plants.

It is also known that the class of emulsifiers comprising the fatty acid esters of polyoxyethylated sorbitan have proven to be sufficiently compatible with plants. This class of emulsifiers, however, only contribute to a dilution of the product without themselves being effective for the desired purpose. Therefore, the use of these absolutely necessary emulsifiers is not satisfactory in the long run. Hence, the problem of finding new and effective compounds for inhibiting the growth of the cambium of plants, especially the growth of axillary shoots of tobacco plants, which compounds do not need any expensive emulsifiers for the packaging of emulsifiable concentrates.

OBJECTS OF THE INVENTION

An object of the present invention is the development of an at least water-emulsifiable plant growth regulator, especially for inhibiting the growth of sucker shoots of tobacco plants, consisting of fatty acid polyoxyethylene glycol ester mixtures obtained by ethoxylating fatty acids having from 6 to 12 carbon atoms with from 4 to 8 mols of ethylene oxide per mol of fatty acid.

Another object of the present invention is the development of a process for regulating plant growth, especially for inhibiting the growth of sucker shoots of tobacco plants, consisting of the step of wetting said plants with a diluted aqueous media containing from 2% to 10% by weight of an at least water-emulsifiable fatty acid polyoxyethylene glycol ester mixtures obtained by ethoxylating fatty acids having from 6 to 12 carbon atoms with from 4 to 8 mols of ethylene oxide per mol of fatty acid.

These and other objects of the invention will become more apparent as the description thereof proceeds.

DESCRIPTION OF THE INVENTION

The drawbacks of the prior art have been overcome and the above objects have been achieved in that for regulating the growth of plants, especially for inhibiting the growth of axillary or sucker shoots of tobacco plants, substances are used which have a content of fatty acid polyoxyethylene glycol ester mixtures which are obtained when fatty acids having 6 to 12 carbon atoms in the molecule, either singularly or in admixture, are ethoxylated with 4 to 8 mols of ethylene oxide per mol of fatty acid.

More particularly, the present invention relates to a process for regulating plant growth, especially for inhibiting the growth of sucker shoots of tobacco plants, consisting of the step of wetting said plants with a diluted aqueous media containing from 2% to 10% by weight of an at least water-emulsifiable fatty acid polyoxyethylene glycol ester mixtures obtained by ethoxylating fatty acids having from 6 to 12 carbon atoms with from 4 to 8 mols of ethylene oxide per mol of fatty acid; as well as the water-emulsifiable plant growth regulators themselves and the diluted aqueous media containing the same.

The compounds to be used for the preparation of the substances according to the invention are manufactured by the use of the well known addition reaction in which ethylene oxide is added or adducted to fatty acids in the presence of catalysts at elevated temperatures and pressure. Accordingly, when free fatty acids having a chain length of 6 to 12 carbons are caused to react with 4 to 8 mols of ethylene oxide per mol of fatty acid in the presence of catalytic quantities of an alkaline alkoxylation catalyst, preferably an alkali metal lower alkanolate, such as sodium methylate, addition of ethylene oxide occurs, resulting in an equilibrium ester mixture consisting of about 45% to 55% of fatty acid polyoxyethylene glycol monoester, about 25% to 35% of fatty acid polyoxyethylene glycol diester, and about 15% to 25% of free polyoxyethylene glycol. The average polyoxyethylene chain length corresponds to the quantity of ethylene oxide used.

Eligible starting fatty acids for the manufacture of the compounds according to the invention are, for example, capronic acid, oenanthic acid, caprylic acid, pelargonic acid, capric acid, lauric acid, or their mixtures having any percentage composition whatsoever. Particularly suitable compounds are the fatty acids having 8 to 10 carbon atoms, such as caprylic acid, pelargonic acid, capric acid, and mixtures which contain predominant quantities of these acids.

When 4 to 8 mols of ethylene oxide per mol of fatty acid are added to a fatty acid mixture having an arbitrary percentage composition of capronic acid, caprylic acid, capric acid, and lauric acid or when this quantity of ethylene oxide is added to individual pure acids in this carbon chain range, then, products are obtained which are self-emulsifiable in water. That is, when these compounds are diluted with water, they form emulsions spontaneously or they form stable solubilizates in the range of 6 to 8 mols of ethylene oxide per mol of fatty acid.

When the emulsions or solubilizates thus obtained are applied to tobacco plants using concentrations customary for plant growth regulators of 4% to 6% of effective substance in water, these emulsions or solubilizates show a good inhibitory effect with respect to the axillary shoots of tobacco plants. Young shoots of less than 2 cm length are destroyed, whereas the growth of older shoots is inhibited to a large extent. This concentration of the emulsions or solubilizates does not in any way damage the tobacco leaves themselves.

As to fat derivatives, the only satisfactory inhibitory effect known until now was that of the fatty alcohols and the methyl esters of fatty acids having a chain length of $C_8$ to $C_{12}$. Moreover, the good compatibility with plants of the fatty acid polyoxyethylene glycol ester mixtures to be used according to the invention was surprising since polyoxyethylene glycol fatty alcohol ethers in the same range of chain length cause strong damage to tobacco plants even when only employed as emulsifiers in an amount of about 10% to 30% by weight of the effective substance.

In order to regulate plant growth, especially to inhibit the growth of axillary shoots of tobacco plants, an effective quantity of the fatty acid polyoxyethylene glycol ester mixtures to be used according to the invention is applied to the plants. These mixtures are employed in application to the plants in the form of a diluted aqueous emulsion. For the preparation of the ready-to-be used emulsions or solubilizates, the compounds according to the invention are so far diluted with water that the effective content amounts to 2% to 10% by weight, preferably 4% to 6% by weight.

Moreover, the products to be applied according to the invention can contain additional products, such as are used for the treatment of plants. These additives can be incorporated to the extent that the formation of the emulsion is not impaired. Examples of such products for the treatment of plants are, for example, leaf nutrients, insecticides, ripening agents, fungicides and in certain cases, other plant growth regulators.

The substances according to the invention prevent or inhibit very effectively the growth of axillary or sucker shoots or tobacco plants. Beyond that, they can also be applied for inhibiting the growth of the cambium of decorative plants.

The ready-to-use emulsions or solubilizates can be applied to the tobacco plants according to the conventional procedures by spraying or brushing. Before the treatment, if so desired, the larger axillary shoots can be removed by hand, and the tobacco plants can be trimmed. In general, it is sufficient that the substances according to the invention are applied once in the form of a diluted emulsion in order that the growth of the axillary shoots is sufficiently inhibited or prevented. In many cases, a second treatment may be advantageous, but should not be carried out until a time period of 8 to 14 days has passed. The quantity of the ready-to-use 4% to 6% emulsion to be applied per tobacco plant can fluctuate within wide limits and might vary between 30 gm to 60 gm. In general, an effective level of spraying is attained when the spray emulsion runs off from the tobacco leaves in drops, where care is also to be taken that first of all, the plant stem is sufficiently coated with the emulsion since the axillary shoots grow therefrom.

EXAMPLES

The following examples explain the object of the invention in greater detail without limiting the scope of the invention in any manner.

EXAMPLE 1

In an autoclave, 3 gm of a 30% sodium methylate solution in methanol were added to 418 gm of a fatty acid distillation forerun, which was a mixture comprised of about 2% capronic acid, 45% caprylic acid, 45% capric acid, and 8% lauric acid. Methanol was removed by distillation under vacuum at 100°C for 15 minutes. The mixture thus obtained was heated to 150°C, and ethylene oxide was pressed in under a pressure of 10 atm. gauge. By use of this method known per se, 528 gm of ethylene oxide were added, which corresponds to a quantity of about 5 mols of ethylene oxide per mol of fatty acid.

The reaction product thus obtained was spontaneously emulsifiable in water. When a 5% emulsion of the above-named fatty acid polyoxyethylene glycol ester mixture was used for the spraying of tobacco plants at a level whereby the emulsion dripped off the leaves, a dying of the axillary shoots could be ascertained after one week. A partial additional growth of the shoots could be observed only in lower axils which evidently were not reached by the spray.

EXAMPLE 2

According to the particulars given in Example 1, 432 gm of caprylic acid were caused to react with 730 gm of ethylene oxide, which corresponds to about 5.5 mols of ethylene oxide per mol of fatty acid. The reaction product thus obtained was spontaneously emulsifiable in water and when applied in the form of a 5% emulsion, gave the good results with reference to the growth inhibition of the axillary shoots of tobacco plants as the product of Example 1.

EXAMPLE 3

According to the particulars in Example 1, 516 gm of capric acid were caused to react with 850 gm of ethylene oxide, which corresponds to a quantity of about 6.5 mols of ethylene oxide per mol of fatty acid. When the reaction product thus obtained was stirred into water, a slightly clouded solubilizate resulted. The aqueous solution containing about 5% effective substance was used for the spraying of tobacco plants which were about 15 weeks old, and the spraying was continued until the emulsion dripped off the tobacco leaves. By the use of this treatment, the growth of axillary shoots was alsmot completely prevented.

The preceding specific embodiments are illustrative of the practice of the invention. It is to be understood, however, that other expedients known to those skilled in the art or disclosed herein, may be employed without departing from the spirit of the invention or the scope of the appended claims.

We claim:
1. An at least water-emulsifiable plant growth regulator for inhibiting the growth of sucker shoots of tobacco plants, consisting of fatty acid polyoxyethylene glycol ester mixtures obtained by ethoxylating fatty acids having from 6 to 12 carbon atoms with from 4 to 8 mols of ethylene oxide per mol of fatty acid, said mixtures consisting of about 45% to 55% by weight of fatty acid polyoxyethylene glycol monoesters, about 25% to 35% by weight of fatty acid polyoxyethylene glycol diesters and about 15% to 25% of free polyoxyethylene glycol.

2. The plant growth regulator fatty acid polyoxyethylene glycol ester mixtures of claim 1 wherein said fatty acids are mixtures of fatty acids having from 6 to 12 carbon atoms.

3. The plant growth regulator fatty acid polyoxyethylene glycol ester mixtures of claim 1 wherein said fatty acids are selected from the group consisting of fatty acids having from 8 to 10 carbon atoms and mixtures of fatty acids having from 8 to 10 carbon atoms.

4. Aqueous emulsions for application to tobacco plants for growth regulation of sucker shoots consisting essentially of water containing from 2% to 10% by weight of the plant growth regulator fatty acid polyoxyethylene glycol ester mixtures of claim 1.

5. The aqueous emulsions of claim 4 having a content of from 4% to 6% by weight of said ester mixtures.

6. A process for inhibiting the growth of sucker shoots of tobacco plants, consisting of the steps of wetting said plants with a diluted aqueous media containing from 2% to 10% by weight of an at least water-emulsifiable fatty acid polyoxyethylene glycol ester mixture obtained by ethoxylating fatty acids having from 6 to 12 carbon atoms with from 4 to 8 mols of ethylene oxide per mol of fatty acid, said mixtures consisting of about 45% to 55% by weight of fatty acid polyoxyethylene glycol monoesters, about 25% to 35% by weight of fatty acid polyoxyethylene glycol diesters and about 15% to 25% of free polyoxyethylene glycol.

7. The process of claim 6 wherein said fatty acids are mixtures of fatty acids having from 6 to 12 carbon atoms.

8. The process of claim 6 wherein said fatty acids are selected from the group consisting of fatty acids having from 8 to 10 carbon atoms and mixtures of fatty acids having from 8 to 10 carbon atoms.

* * * * *